United States Patent [19]

Rassow et al.

[11] 4,125,320
[45] Nov. 14, 1978

[54] RETINOMETER

[75] Inventors: Bernd Rassow, Hamburg; Diethard Wolf, Lubeck; Klaus Korner, Grosshansdorf, all of Germany

[73] Assignee: Optische Werke G. Rodenstock, Germany

[21] Appl. No.: 707,031

[22] Filed: Jul. 20, 1976

[30] Foreign Application Priority Data

Apr. 13, 1976 [DE] Fed. Rep. of Germany ....... 2616139

[51] Int. Cl.² .......................... A61B 3/10; A61B 3/00
[52] U.S. Cl. .................................. 351/13; 351/36; 351/15; 351/11; 351/14
[58] Field of Search .................. 351/13, 15, 14, 6, 30, 351/17, 32, 36, 37, 11; 356/113; 350/96 R

[56] References Cited

U.S. PATENT DOCUMENTS

| | | | |
|---|---|---|---|
| 1,806,318 | 5/1931 | Tillyer | 351/11 |
| 2,428,975 | 10/1947 | Lamb | 350/96 R |
| 3,536,381 | 10/1970 | Pituley | 350/203 |
| 3,652,153 | 3/1972 | Gambs | 351/14 |
| 3,942,879 | 3/1976 | Pledger | 350/6 |
| 3,969,020 | 7/1976 | Lynn | 351/17 |
| 4,009,940 | 3/1977 | Ohzu | 351/113 |

OTHER PUBLICATIONS

P. Hariharan, Applied Optics, vol. 14, No. 5, May 1975, pp. 1056, 1057.

Primary Examiner—Paul A. Sacher
Assistant Examiner—Rodney B. Bovernick
Attorney, Agent, or Firm—Craig & Antonelli

[57] ABSTRACT

A laser interference instrument for determination of the visual acuity of the human eye includes an interference optical system for producing an interference light pattern mounted on a slit lamp microscope disposed on an instrument support that is finely adjustable horizontally and in height. The interference optical system includes a laser light source and a rotatable turntable carrying a plurality of plane parallel plates or wedge plates which may be selectively moved into the light path of the laser light source to produce different interference patterns to be projected onto the human eye and which are then observable through the slit lamp microscope.

19 Claims, 7 Drawing Figures

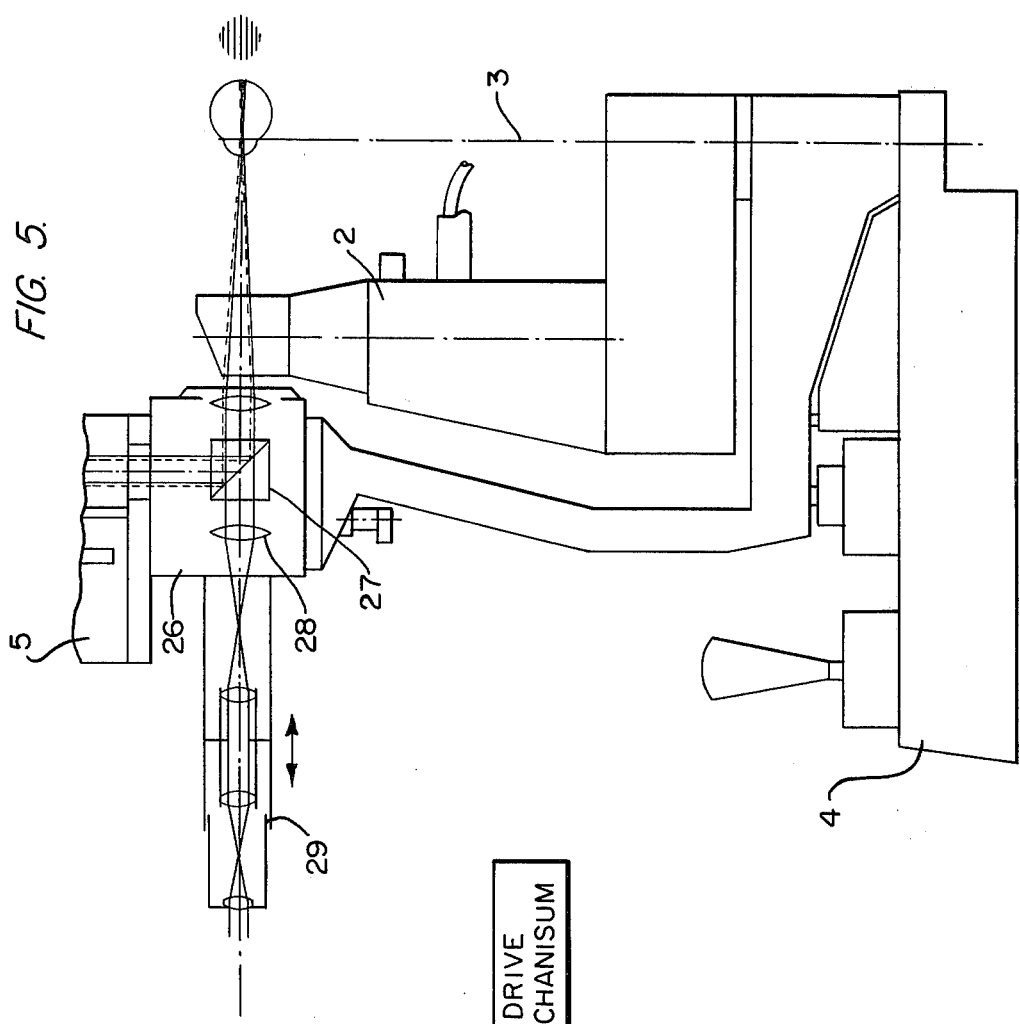
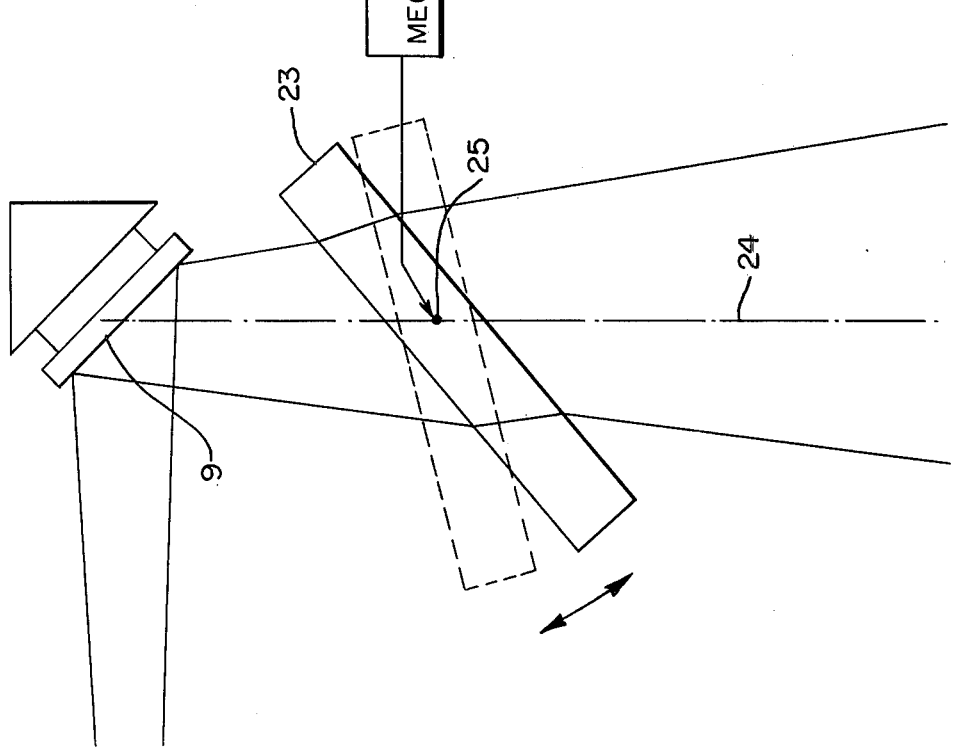

RETINOMETER

The invention relates to a laser interference instrument for determination of the visual acuity of the human eye.

German Offenlegungsschrift No. 21 21 873 discloses an objective ocular refractometer, wherein a sinusoidal strip test grid, which is created on the retina by interference of two laser beams through the optical part of the eye that is to be examined, is formed externally, and the modulation depth of the test grid produced by the refraction state of the eye is determined. A direct observation of the grid formed on the retina, or of the point of irradiation, is not provided in this arrangement.

The purpose of this invention is to create an instrument for measurement of retinal visual acuity of the human eye where the interference pattern produced by laser interference on the retina is precisely adjustable with reference to its position in the eye, and is directly observable by the physician. Further, the interference pattern in question is to be adjustable in its structure as well as displaceable and rotatable in its position. In addition, the instrument of the invention is to be combinable in a special embodiment with a refractometer device.

This problem is solved by the present invention in that the interference optical system together with the observation optical system is disposed on a traveling instrument support that can be finely adjusted with reference to the eye that is being examined. By virtue of the mechanical combination of the interference optical system with the observation optical system, continuous undisturbed observation of the interference light pattern produced within the eye can be obtained, whereby it is possible to simultaneously provide the indispensable fine adjustment of the instrument with reference to the eye.

In practical use of the instrument of the invention, interference light bands of different thicknesses are produced in the eye of the patient, and the threshold is determined, up to which these bands can be perceived as being separated from one another. Here it is advantageous to begin with a thin line, to make a certain degree of accommodation possible. To verify the patient's statements with respect to the perceived pattern, it is advantageous to change the direction of the band, or to allow the pattern to move out laterally.

A slit lamp microscope is a suitable observation optical system in the framework of the invention. In such a microscope, the pupillary area of the eye under examination is visibly enlarged. In the center of the visual field the fine focusing points of the laser appear in such a way that it is possible to explore the anterior medium of the eye with its points, for cloudiness, and to seek out possible clear zones. For this purpose the fine adjustability of the instrument with reference to the eye that the invention offers is necessary. Such adjustability is advantageously produced in building the instrument in accordance with the invention on a slit lamp that is disposed conventionally together with the slit lamp microscope on a finely adjustable instrument support.

The interference light pattern can be produced by means of a mirror arrangement, deflection on a grid or the like. However, within the scope of the invention, the interference light pattern is produced by means of plane parallel plates or even wedge plates because in this way the necessary mechanical stability of the device is achieved most simply. The light beam, emitted advantageously by a helium-neon laser, is reflected on the front and rear surface of the plates so that the two necessary mutually coherent bundles are produced that are mutually displaced, corresponding to the thickness of the plane parallel plates. Thin platelets give a thin line, while greater thicknesses are obtained with thicker plates.

According to the invention, a number of glass plates of different thicknesses can be disposed on a common support or holder, advantageously a turntable, so that they can be swung in individually into the path of the beam. The position of the plates with reference to each other must be so adjusted that their midplane in the swung-in position is at the same height, to ensure that the interference pattern produced by the individual plates will appear at the same place on the retina. Further, there may be a rotating prism, e.g., a Dove or Pechan prism, disposed in the interference beam path, in order to be able to vary the direction of the interference light pattern.

It is also desirable to shift the interference light pattern laterally or to allow it to swing. For this a plane parallel plate or reflecting surface, advantageously pivotable about two axes, may advantageously be disposed in the path of the beam. By a movement of the interference light pattern transversely to the band structure, nystagmus can be provoked, as long as the eye can perceive a structure of the light pattern. In this way it is objectively determinable whether or with what structure of the interference light pattern the examined eye can still recognize the pattern. Ordinary electromechanical drives can be provided to move the deflecting optical system.

The instrument of the invention can additionally be so constructed in the framework of the observation optical system that the interference light pattern from the eye can be defined externally with maximum adjustment for contrast. The change in power of refraction that is necessary to get maximum contrast constitutes an objective value for assessing the refraction state of the examined eye. The change of the refraction power of the observation optical system can be effected by exchange of defined lenses or by the setting of a vario-optic or variable power optical system.

These and other features and advantages of the subject invention will be described in greater detail with reference to the accompanying drawings, wherein:

FIG. 4 is a schematic representation of the beam path in the zone of the deflecting optical system;

FIG. 5 is a side view of an instrument in accordance with the invention combined with a refractometer.

Figure 1:
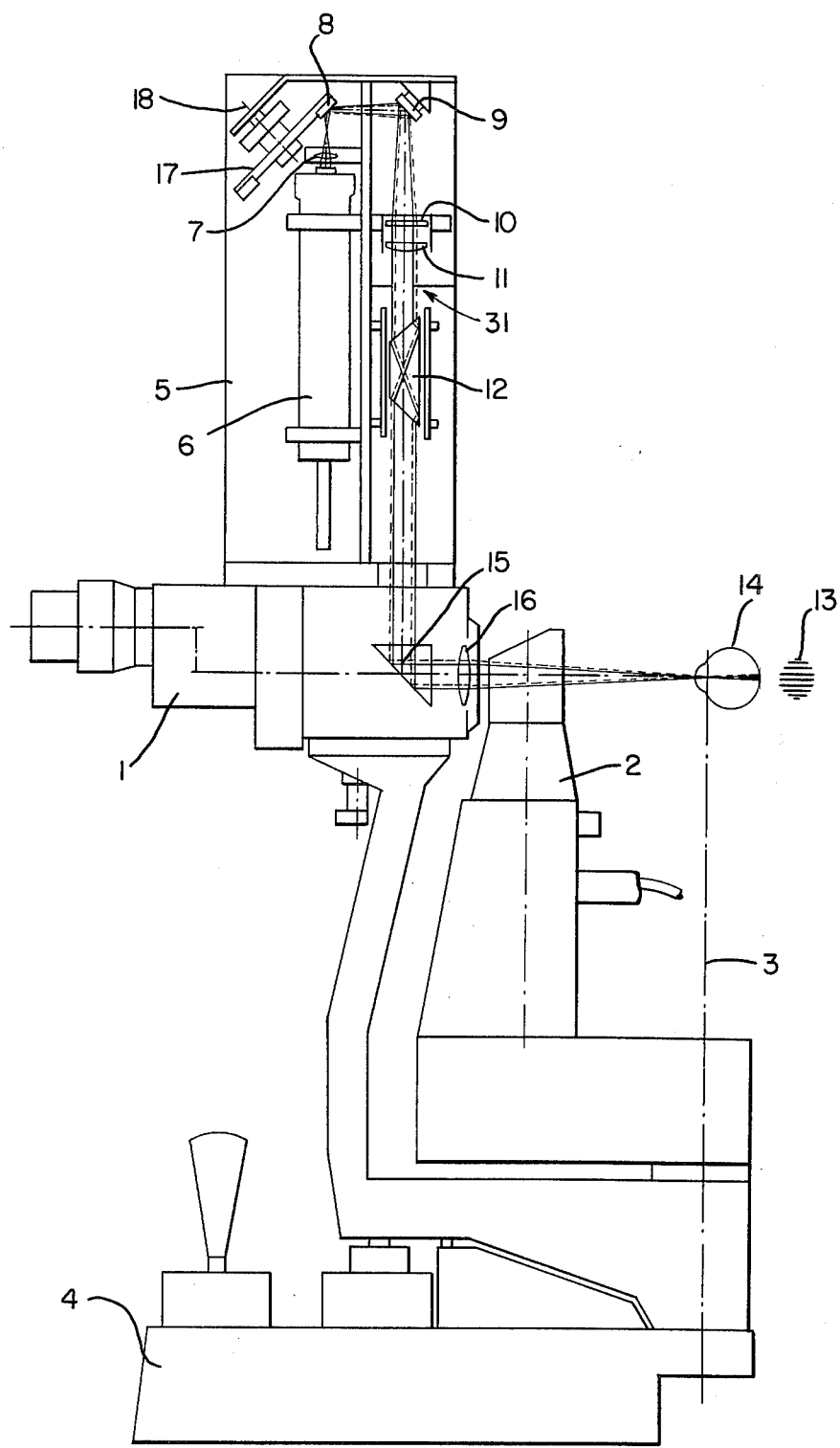
FIG. 1 is a side view, partly cut away, of an instrument of the invention.

In particular, FIG. 1 shows a slit lamp microscope 1 which, like slit lamp 2, is pivotable about a vertical shaft 3. Slit lamp microscope 1 and slit lamp 2 of known type are disposed on an instrument support 4, also of known type, that is finely adjustable horizontally and in height. In accordance with the present invention, the laser interference optical system 5 is disposed on the slit lamp microscope 1.

A laser light source 6 is provided in the system 5, and may take the form of a helium-neon laser, e.g., Hughes model 3221 H-PC. To produce a sufficiently large visual field of about 2°, the laser beam from laser light source 6 is focused through a lens 7 that has a focal length of about 20 mm, and is thereby partly spread out behind the focus. The focused beam is then directed to a plane parallel plate 8 disposed at a suitable angle to the beam path. By reflection on the upper and lower surfaces of plane parallel plate 8, two interfering laser beams are produced that are reflected horizontally and then downwardly reflected via an adjustable deflecting mirror 9.

The laser light bundles which are reflected from mirror 9 then penetrate an attenuating filter 10 and a collecting lens 11, that may have a focal length of about 150 mm and serves to make the two laser beams parallel. An aperture or slit 31 may be disposed in the beam path at a distance of the focal length ahead of the collecting lens. The parallel laser beams then pass through a prism 12, for example, a Dove or Pechan prism, which is mounted for rotation about its axis. With use of rotary prism 12, the interference light pattern on the subject's fundus can be turned in its plane. For reflecting the interference light pattern 13 in the eye 14, there is provided in the microscope 1 a deflecting prism 15 for turning the interference light pattern along the axis of microscope 1, as well as a lens 16 that acts as an objective. With this arrangement, the interference light pattern in the eye 14 can be precisely observed by means of slit lamp microscope 1.

Figure 2:
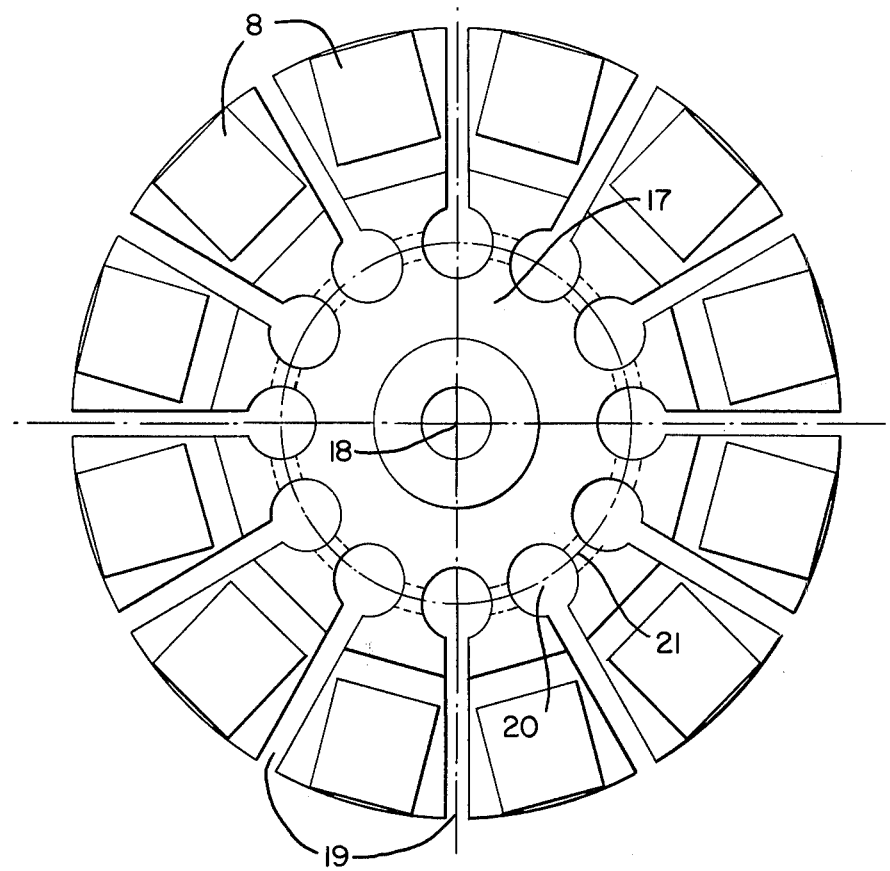
FIG. 2 is a detail axial view of the support, made as a turntable, for a plurality of plane plates.

Plane parallel plate 8 is disposed on a turntable 17 along with a plurality of additional plane parallel plates, the said turntable being rotatable about a shaft 18. Turning may be accomplished manually, or by means of a remote-controlled step motor. FIG. 2 shows turntable 17 of FIG. 1 on a larger scale, in the direction of shaft 18. In the peripheral zone of turntable 17 a plurality of plane parallel plates 8 are fixed, e.g., cemented on. Between the individual plane plates, turntable 17 is provided with notches 19 that run out in holes 20, so that there are narrow crosspieces 21 which allow pecise adjustment of the axial position of the plane parallel plates 8, by bending the support in the zone of the crosspieces.

Figure 3A:
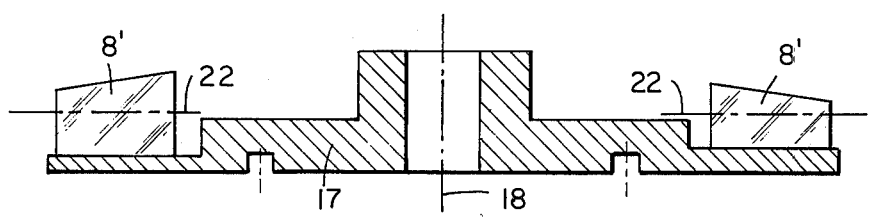
FIG. 3A is an axial section as in FIG. 3 with a modification thereof.
Figure 3:
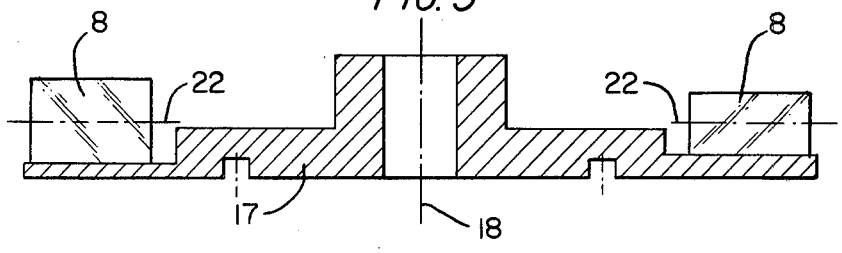
FIG. 3 is an axial section through the turntable of FIG. 2.

In FIG. 3 the turntable 17 of FIG. 2 is shown in section, in the direction of shaft 18. The plane parallel plates 8 are so disposed that their midplanes 22 lie in a common plane. For this purpose, the thickness of the part of turntable 17 which supports each plate 8 may vary to accommodate plates of different thickness.

FIG. 3A shows a similar arrangement to that of FIG. 3, except that wedge plates 8' of variable thicknesses are used.

FIG. 4 shows the path of the laser beams in the zone of deflecting mirror 9 in a modification of the embodiment of FIG. 1. Below deflecting mirror 9 there may be additionally provided a plane parallel plate 23 that is rotatable about vertical axis 24, as well as swingable about axis 25 that runs at a right angle to the plane of the drawing. A swing or swinging movement of plane parallel plate 23 about axis 25 in the illustrated position produces a movement of the interference light pattern 13 in the eye 14, transversely to the direction of the band. After turning of the plane parallel plate 23 by 90° about axis 24, with swinging about axis 25, there is a movement of the interference light pattern in the direction of the band. A drive mechanism, such as an ordinary electromechanical drive, can be provided to move the plate 23.

FIG. 5 shows a modified embodiment of the present invention, where instead of a slit lamp microscope 1 as used in FIG. 1, an observation optical system 26 is provided, that presents a divider system 27 and an imaging lens 28. By means of a movable examining optical system 29, imaging of the interference pattern may be adjusted for maximum contrast. The value of the displacement is a direct measurement of the refraction state of the examined eye.

Figure 6:
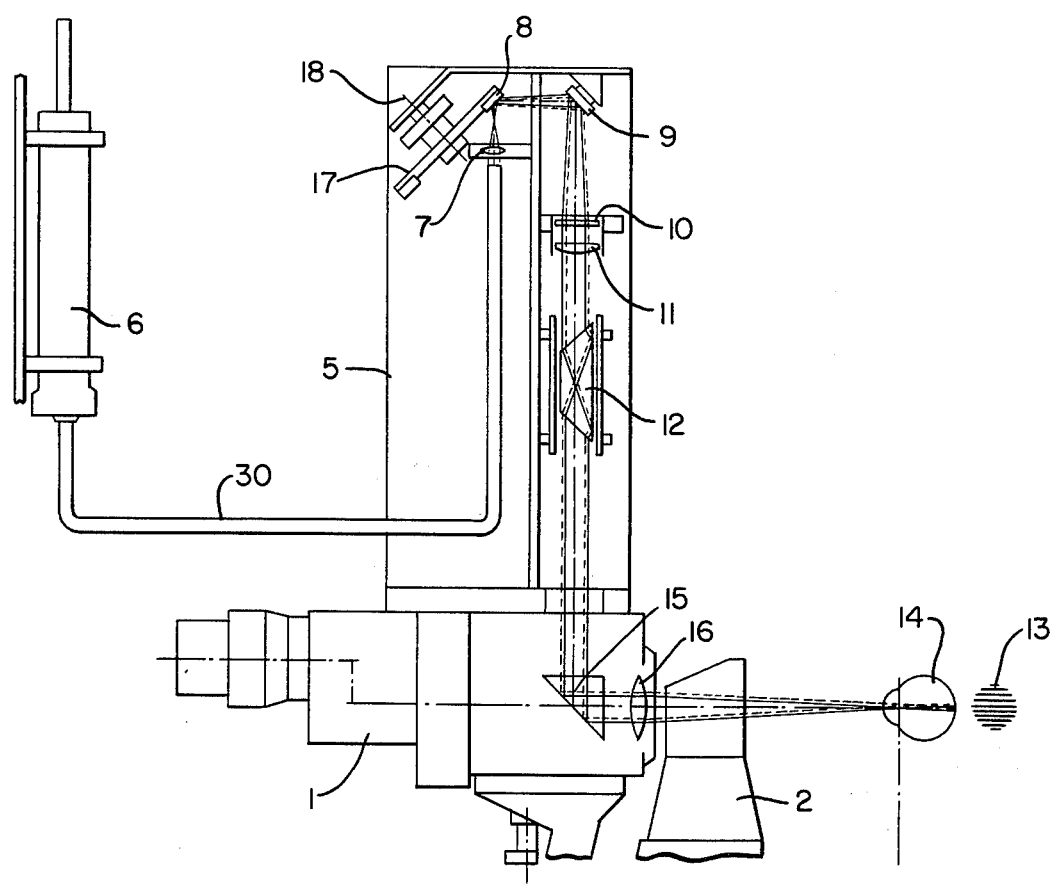
FIG. 6 is a side view of a modification of the instrument of FIG. 1.

FIG. 6 shows a further modified embodiment of the present invention wherein the laser light source 6 is disposed outside of the interference optical system 5 and is connected thereto by a light conducting rod 30. In this way different laser light sources are easily connectable to the instrument which may be usable with other instruments.

While we have shown and described several embodiments in accordance with the present invention, it is understood that the same is not limited thereto but is susceptible of numerous changes and modifications as known to a person skilled in the art, and we therefore do not wish to be limited to the details shown and described herein but intend to cover all such changes and modifications as are obvious to one of ordinary skill in the art.

What is claimed is:

1. A laser interference instrument for measurement of retinal visual acuity of the human eye, comprising a laser light source, interference optical means for projecting an interference light pattern of light from said laser light source on the retina of an eye over two different optical paths, and observation optical means for optically observing the points of irradiation of the interference light pattern on the eye, characterized in that said interference optical means together with said observation optical means are disposed for fine adjustment with reference to the examined eye on a traveling instrument support, wherein said interference optical means includes one plate of a plurality of plates selectively provided in the beam path of said laser light source to double the laser beam provided thereby with reflection occurring on the front and rear surfaces of the said plate, and characterized in that said plurality of plates differ in thickness, and including holder means for selectively moving each plate into the beam path to vary the interference light pattern.

2. A laser interference instrument as defined in claim 1, characterized in that said holder means comprises a rotatable circular disk, said plates being disposed in the peripheral zone of said circular disk which is mounted to be rotatable.

3. A laser interference instrument as defined in claim 2, characterized in that said circular disk is provided with radial slits disposed between the plates, in such a way that the plates are individually adjustable as to position axially of the disk by bending the circular disk segments that support them.

4. A laser interference instrument as defined in claim 1, characterized in that said interference optical means further includes a rotary prism disposed in the beam path of said laser light source downstream of said plate to turn the interference light pattern.

5. A laser interference instrument as defined in claim 1, characterized in that said interference optical means further includes a collecting lens disposed in the beam path of said laser light source to focus the laser beam on or at the height of said plate.

6. A laser interference instrument as defined in claim 5, characterized in that said interference optical means further includes a slit disposed in the beam path at a distance of a focal length ahead of said collecting lens.

7. A laser interference instrument as defined in claim 1, characterized in that said observation optical means comprises a slit lamp microscope on which said interference optical means i disposed.

8. A laser interference instrument as defined in claim 1, characterized in that said laser light source is fixedly connected to said interference optical means.

9. A laser interference instrument as defined in claim 1, characterized in that said laser light source is connected via a light conducting cable to said interference optical means.

10. A laser interference instrument as defined in claim 1, wherein said interference optical means further comprises deflecting optical means for movement of a band-like interference light pattern transversely to and in the direction of the band in the beam path.

11. A laser interference instrument as defined in claim 10, characterized in that said deflecting optical means comprises a plane parallel plate mounted for pivotable movement about at least one axis.

12. A laser interference instrument as defined in claim 11, characterized in that said pivotable plate of said deflecting optical means is connected with a regulatable mechanical drive.

13. A laser interference instrument as defined in claim 1, characterized in that said observation optical means is adjustable for objective determination of the erroneous vision of the examined eye, defined at maximum contrast of the observed pattern.

14. A laser interference instrument as defined in claim 13, further including means for adjusting the refraction of said observation optical means.

15. A laser interference instrument as defined in claim 13, characterized in that said observation optical means includes a variable power optical system.

16. A laser interference instrument as defined in claim 1, wherein each said plate is a plane parallel plate.

17. A laser interference instrument as defined in claim 1, wherein each said plate is a wedge plate.

18. A laser interference instrument for measurement of retinal visual acuity of the human eye, comprising a laser light source, interference optical means for projecting an interference light pattern of light from said laser light source on the retina of an eye over two different optical paths, characterized in that said interference optical means comprises one of a plurality of plane parallel plates of differing thicknesses or a plurality of wedge plates of differing thicknesses for duplicating a laser light beam from said laser light source into said two different optical paths by effecting reflection at the front and rear faces of a given plate, each of said plates being selectively insertable into the path of said laser light beam to vary the interference light pattern.

19. A laser interference device as defined in claim 18, characterized in that said interference optical means is provided with observation optical means for optically observing the points of irradiation of the interference light pattern on the eye and the focus of the two laser light beams, and wherein said interference optical means and said observation optical means are mounted together on a finely adjustable instrument support to be precisely adjustable with respect to the eye to be examined.

* * * * *